United States Patent
Ben Chaabane et al.

(10) Patent No.: US 9,885,027 B2
(45) Date of Patent: Feb. 6, 2018

(54) PROCESS FOR THE PRODUCTION OF AN ENZYMATIC COCKTAIL USING SOLID RESIDUES FROM A PROCESS FOR THE BIOCHEMICAL COVERSION OF LIGNOCELLULOSIC MATERIALS

(71) Applicant: IFP Energies nouvelles, Rueil-Malmaison (FR)

(72) Inventors: Fadhel Ben Chaabane, Paris (FR); Sylvain Louret, Lyons (FR)

(73) Assignee: IFP ENERGIES NOUVELLES, Rueil-Malmaison (FR)

( * ) Notice: Subject to any disclaimer, the term of this patent is extended or adjusted under 35 U.S.C. 154(b) by 137 days.

(21) Appl. No.: 14/365,274

(22) PCT Filed: Nov. 27, 2012

(86) PCT No.: PCT/FR2012/000489
§ 371 (c)(1),
(2) Date: Jun. 13, 2014

(87) PCT Pub. No.: WO2013/087998
PCT Pub. Date: Jun. 20, 2013

(65) Prior Publication Data
US 2014/0349373 A1 Nov. 27, 2014

(30) Foreign Application Priority Data
Dec. 14, 2011 (FR) ...................................... 11 03857

(51) Int. Cl.
C12N 9/42 (2006.01)
C12N 1/16 (2006.01)
C12N 9/24 (2006.01)
C12P 7/10 (2006.01)
C12P 21/00 (2006.01)

(52) U.S. Cl.
CPC ............. *C12N 9/2437* (2013.01); *C12N 1/16* (2013.01); *C12N 9/2477* (2013.01); *C12P 7/10* (2013.01); *C12P 21/00* (2013.01); *C12Y 302/01004* (2013.01); *C12Y 302/01074* (2013.01); *C12P 2203/00* (2013.01); *Y02E 50/16* (2013.01)

(58) Field of Classification Search
CPC .. C12N 9/2437; C12N 9/248; C12N 2501/70; Y02E 50/16; Y02E 50/17; Y02E 50/13; Y02E 50/343
See application file for complete search history.

(56) References Cited

U.S. PATENT DOCUMENTS

| 3,972,775 A * | 8/1976 | Wilke ..................... C12P 19/14 435/163 |
| 2006/0177917 A1 * | 8/2006 | Warzywoda ......... C12N 9/2437 435/161 |
| 2011/0236954 A1 * | 9/2011 | Ben Chaabane ........ C12N 1/14 435/200 |

FOREIGN PATENT DOCUMENTS

EP 1690944 A1 8/2006
EP 2371950 A1 10/2011

OTHER PUBLICATIONS

Sukumaran et al. Microbial cellulases—production, applications and challenges. J Sci Ind Res. 2005;64:832-844.*
Pourquie et al. Scale up of cellulase production and utilization. Biochemistry and Genetics of Cellulose Degradation. 1988;71-86.*
Mukhopadhyay et al. Bioconversion of water hyacinth hydrolysate into ethanol. BioResourses. 2010;5(2):1301-1310.*
Shrestha, P. et al., "Enzyme production by wood-rot and soft-rot fungi cultivated on corn fiber followed by simultaneous saccharificiation and fermentation," Journal of Agricultural and Food Chemistry, 2009, vol. 57, pp. 4156-4161.
Chahal, P. S. et al., "Production of cellulase in solid-state fermentation with trichoderma reesei MCG 80 on wheat straw," Applied Biochemistry and Biotechnology, 1996, vol. 57/58, pp. 433-442.
Chahal, D. S. et al., "Solid-state fermentation with trichoderma reesei for cellulase production," Applied and Environmental Microbiology, 1985, vol. 49, No. 1, pp. 205-210.
International Search Report for PCT/EP2012/000489 dated Apr. 25, 2013.

* cited by examiner

*Primary Examiner* — Lynn Y Fan
(74) *Attorney, Agent, or Firm* — Millen White Zelano and Branigan, PC; John Sopp; Csaba Henter

(57) ABSTRACT

The present invention concerns a process for the production of an enzymatic cocktail by submerged culture with a cellulolytic microorganism, comprising two phases:
  a phase a) for growth of said microorganism in the presence of at least one carbonaceous growth substrate in a closed reactor, said growth phase being carried out with a concentration of carbonaceous growth substrate in the range 10 to 90 g/L;
  a phase b) for the production of the enzymatic cocktail, in which at least one carbonaceous inducer substrate is supplied, said carbonaceous inducer substrate being at least one solid residue obtained from the step for enzymatic hydrolysis of lignocellulosic materials which have undergone a pre-treatment step, said production phase being carried out with a concentration of carbonaceous production substrate in the range 150 to 400 g/L.

14 Claims, No Drawings

PROCESS FOR THE PRODUCTION OF AN ENZYMATIC COCKTAIL USING SOLID RESIDUES FROM A PROCESS FOR THE BIOCHEMICAL COVERSION OF LIGNOCELLULOSIC MATERIALS

FIELD OF THE INVENTION

The present invention concerns the production of cellulolytic and hemicellulolytic enzymes, in particular in the context of the production of ethanol from cellulosic or lignocellulosic materials.

PRIOR ART

Since the 1970s, the transformation of lignocellulosic materials into ethanol after hydrolysis of the constituent polysaccharides into fermentable sugars has been the focus of a great many studies. Examples which may be studied are the reference works from the National Renewable Energy Laboratory (Process Design and Economics for Biochemical Conversion of Lignocellulosic Biomass to Ethanol, Humbird et al., NREL/TP-5100-57764, May 2011).

Lignocellulosic materials are cellulosic materials, i.e. containing more than 90% by weight of cellulose, and/or lignocellulosic materials, i.e. constituted by cellulose, hemicelluloses, which are polysaccharides essentially constituted by pentoses and hexoses and lignin, which is a macromolecule with a complex structure and a high molecular weight, composed of aromatic alcohols bonded via ether bonds.

Wood, straw and corn cobs are the most widely used lignocellulosic materials, but other sources, dedicated forest cultures, residues of alcoholigenic sugar and cereal plants, products and residues from the papermaking industry and transformation products of cellulosic and lignocellulosic materials may be used. They are mostly constituted by approximately 35% to 50% of cellulose, 20% to 30% of hemicellulose and 15% to 25% of lignin.

The process for the transformation of lignocellulosic materials into ethanol comprises a step for physico-chemical pre-treatment followed by a step for enzymatic or chemical hydrolysis, a step for ethanolic fermentation of the liberated sugars, the ethanolic fermentation and enzymatic hydrolysis possibly being carried out simultaneously, and a step for recovering the ethanol.

The pre-treated material is hydrolysed either using an acid pathway or using an enzymatic pathway with the use of cellulolytic and/or hemicellulolytic enzymes.

The acid pathway, carried out with the aid of a strong acid, in particular sulphuric acid, is effective but requires large quantities of chemical products (acid then base for neutralization). Enzymatic hydrolysis does not suffer from this disadvantage: it is also carried out under mild conditions and is efficient. In contrast, the cost of the enzymes is still high, representing 30% to 50% of the costs for transformation of the lignocellulosic material into ethanol. For this reason, a great many studies have been carried out in order to reduce this cost: optimization of the enzyme production initially, by selecting hyperproductive strains and by improving the processes for the production of said enzymes, then reducing the quantity of enzymes in hydrolysis, by optimizing the pre-treatment phase or by improving the specific activity of those enzymes.

However, the reduction in the quantity of enzymes may result in non-conversion of a large fraction of the cellulose, involving the production of a large quantity of solid residue obtained from the enzymatic hydrolysis step and/or fermentation step. The same effect is observed if the enzymatic hydrolysis is carried out with a high dry matter content, the dry matter content of a sample, expressed as the percentage by weight, being the ratio of the mass of the sample obtained after drying at 105° C. for 24 hours to the initial mass of the sample. This solid residue then has to be re-treated, conventionally by combustion to produce steam and electricity, or by methanation to produce a biogas.

During the last decade, the principal studies have been aimed at understanding the mechanisms of action of the cellulases and the expression of enzymes in order to excrete the enzymatic cocktail which is the most appropriate to hydrolysis of the lignocellulosic substrates by modifying the strains with molecular biology tools.

The enzymatic cocktail is a mixture of cellulolytic and/or hemicellulolytic enzymes. The enzymes of the enzymatic cocktail contain three main types of activities: endoglucanases, exoglucanases and cellobiases, these latter also being known as β-glucosidases.

The microorganism which is the most widely used for the production of the enzymatic cocktail is the fungus *Trichoderma reesei*. In the presence of an inducer substrate, for example cellulose, wild strains have the ability to excrete the enzymatic cocktail considered to be the most suitable for hydrolysis of the cellulose. Other proteins having properties which are indispensable to the hydrolysis of lignocellulosic materials are also produced by *Trichoderma reesei*, for example xylanases. The presence of an inducer substrate is indispensable to the expression of cellulolytic and/or hemicellulolytic enzymes. The nature of the carbonaceous inducer substrate has a considerable influence on the composition of the enzymatic cocktail. This is the case with xylose which, when associated with a carbonaceous inducer substrate such as cellulose or lactose, can significantly improve the activity termed xylanase activity.

Lactose remains one of the most appropriate substrates in the industrial process for the production of enzymatic cocktail; however, its cost varies widely and represents approximately one to two thirds of the cost price of the enzymes. When lactose is used as the source of carbon, the enzymatic cocktail production process is dependent on an external source of carbon. For this reason, the use of carbonaceous substrates obtained from a process for the biochemical conversion of lignocellulosic materials is a major advance if the source of inducer carbon is readily available.

Patent application EP 1 690 944 A1 discloses the use of the aqueous phase obtained after alcoholic fermentation and separation of ethanol as the source of inducer carbon and growth for the culture of cellulolytic microorganism and the production of enzymes. The residue obtained in the bottom of the distillation column is termed "slop". It is filtered and the soluble portion is used for the production of cellulases.

Patent application WO 09 026716 A1 describes the production of an enzymatic cocktail from *Trichoderma reesei* starting from a carbonaceous substrate containing inducer sugars from the production of cellulases. This application discloses that 3% by weight of inducer sugars are sufficient to induce the production of cellulases. The inducer sugars described are mono-, di- and oligo-saccharides possibly produced by the hydrolysis of cellulose.

Patent application WO 11 028554 discloses the use of a biomass which has undergone an acid treatment to cultivate a microbe for the production of cellulases, as well as the use of a solid residue obtained from hydrolysis of the hemicelluloses. This solid residue has been freed from its lignin fraction in a lignin extraction step. The delignified solid residue is used right from the microorganism growth phase, which induces operational difficulties since the viscosity of the medium is high until the production of enzymes has been initiated.

Lignin, in particular the phenolic compounds of which it is composed, is known to have an inhibiting effect on the enzymes (see "Inhibition of enzymatic cellulolysis by phenolic compounds", Tejirian and Xu, Enzyme and Microbial Technology vol. 48 (3) pp. 239-247, Mars 2011).

U.S. Pat. No. 3,972,775 discloses the production of cellulolytic microorganism and enzymes from sugar liquor obtained from the hydrolysate and a cellulosic inducer (for example the ground cellulosic feed). The feed and the cellulosic inducer are cellulosic waste material and thus do not contain lignin.

Patent GB 1 489 145 discloses the culture of cellulolytic microorganism and the production of enzymes from cellulose residues, these latter being obtained from pure cellulosic materials or cellulosic waste. Thus, they do not derive directly from the process for the conversion of the lignocellulosic material.

One aim of the invention is to propose a source of inducer carbon which is readily available, which can produce an enzymatic cocktail with activities appropriate for hydrolysis of the lignocellulosic material. This invention can also be used for initial upgrading of co-products which cannot be upgraded to ethanol.

SUMMARY AND ADVANTAGE OF THE INVENTION

The present invention concerns a process for the production of an enzymatic cocktail by a cellulolytic microorganism, characterized in that it uses a solid residue from the enzymatic hydrolysis of lignocellulosic materials which have undergone a pre-treatment step and optionally a solid residue from the ethanolic fermentation of enzymatic hydrolysates of said materials.

One advantage of the invention is to reduce or dispense with the addition of carbonaceous substrate of external origin to the biochemical process for the conversion of lignocellulosic materials. Another advantage is that solid residues from said biochemical conversion process for the production of an enzymatic cocktail are upgraded. This upgrading means that the quantity of effluents produced which have to be re-treated before discharge or storage can be reduced.

Since said solid residues containing cellulose and lignin are upgraded for the production of an enzymatic cocktail, the cost of said cocktail is reduced. Further, said residues can be used in an upgrade pathway because of the process of the invention, and so just partial hydrolysis can be carried out in the enzymatic hydrolysis step, obtained by reducing the quantity of enzymatic cocktail used in said hydrolysis step. This latter effect also results in a reduction of the cost of the process for the biochemical conversion of the lignocellulosic material.

The invention is all the more advantageous when the treated lignocellulosic materials are refractory to enzymatic hydrolysis (for example poplar or miscanthus).

An additional advantage of the process of the invention is that an enzymatic cocktail is produced which is particularly suitable for enzymatic hydrolysis of the pre-treated lignocellulosic material converted in the biochemical conversion process. Said residues, although they have a high lignin content, surprisingly have an inducer effect, allowing said enzymatic cocktail to be produced.

DETAILED DESCRIPTION OF THE INVENTION

The present invention concerns a process for the production of an enzymatic cocktail with a cellulolytic microorganism, comprising two phases:

a phase a) for growth of said microorganism in the presence of at least one carbonaceous growth substrate in a closed reactor, said growth phase being carried out with a concentration of carbonaceous growth substrate in the range 10 to 90 g/L;

a phase b) for the production of the enzymatic cocktail, in which at least one carbonaceous inducer substrate is supplied, said carbonaceous inducer substrate being at least one solid residue obtained from the step for enzymatic hydrolysis of lignocellulosic materials which have undergone a pre-treatment step, optionally with at least one solid residue obtained from the step for ethanolic fermentation of enzymatic hydrolysates, said production phase being carried out with a concentration of carbonaceous production substrate in the range 150 to 400 g/L.

Said process for the production of an enzymatic cocktail is carried out using submerged culture. The term "submerged culture" means culture in a liquid medium.

The microorganism used in the process for the production of an enzymatic cocktail of the invention are strains of fungi belonging to the genera *Trichoderma, Aspergillus, Penicillium* or *Schizophyllum*, preferably belonging to the species *Trichoderma reesei*. The best performing industrial strains are strains belonging to the species *Trichoderma reesei*, modified to improve the enzymatic cocktail by mutation-selection processes such as, for example, the strain IFP CL847 (French patent FR-B-2 555 803). Strains improved by genetic recombination techniques may also be used. These strains are cultivated in stirred, aerated reactors under conditions compatible with their growth and the production of enzymes.

The carbonaceous growth substrate for said microorganism used in said growth phase a) of the process of the invention is advantageously selected from soluble industrial sugars, preferably from glucose, lactose, xylose, liquid residues obtained after ethanolic fermentation of monomeric sugars from enzymatic hydrolysates of lignocellulosic materials and extracts from the hemicellulosic fraction in the form of monomers obtained from the pre-treated lignocellulosic substrate, used alone or as a mixture. Depending on its nature, said carbonaceous growth substrate is introduced into the closed reactor before sterilization or is sterilized separately and introduced into the closed reactor after sterilization of the latter.

In accordance with the invention, said carbonaceous growth substrate is used in said growth phase a) at an initial concentration in the range 10 to 90 g of carbonaceous substrate per litre of reaction volume.

Preferably, said growth phase a) is carried out for a period in the range 30 to 70 h, preferably in the range 30 to 40 h.

Preferably, said growth phase a) is operated at a pH of 4.8 and at a temperature of 27° C.

In accordance with the invention, said carbonaceous inducer substrate used in said production phase b) is advantageously at least one solid residue obtained from the step for enzymatic hydrolysis of lignocellulosic materials which have undergone a pre-treatment step and/or at least one solid residue obtained from the step for ethanolic fermentation of enzymatic hydrolysates.

Said solid residue is preferably obtained after a partial enzymatic hydrolysis, i.e. when this latter is operated at a high dry matter (DM) content and/or with a small quantity of enzymatic cocktail. The term "high DM content" means more than 20% by weight DM. The term "small quantity of enzymatic cocktail" means less than 10 mg of enzymatic cocktail per g of cellulose in the lignocellulosic material which has undergone a pre-treatment step. The term "partial hydrolysis" means that only 20% to 70% by weight of the cellulose at the inlet to the hydrolysis step is hydrolysed.

Said solid residue is advantageously separated from the effluent of the enzymatic hydrolysis step, and when it is used, from the effluent of the ethanolic fermentation step. The separation is advantageously carried out by filtration, centrifuging or any other method which is known to the skilled person allowing separation of a solid phase and a liquid phase.

Thus, said solid residue is obtained directly from the process for the biochemical conversion of lignocellulosic materials.

Said solid residue comprises a solid portion and a liquid portion. Depending on the separation method used, the solid fraction of the solid residue represents 10% to 40% by weight of solid residue. Said solid fraction is constituted by lignin, mineral compounds and non-hydrolysed cellulose. The fraction of cellulose in said solid portion is 10% to 50% by weight. The fraction of lignin in said solid portion is 45% to 80% by weight. The fraction of mineral compounds in said solid portion is 1% to 15% by weight. The liquid fraction of said solid residue contains xylose (not fermented by the *Saccharomyces cerevisiae* yeast) which is an inducer of xylanase production.

Preferably, said carbonaceous inducer substrate is used as a mixture with at least one other carbonaceous substrate.

Preferably, said other carbonaceous substrate is selected from inducer or non-inducer sugars, preferably selected from lactose, glucose, cellulosic hydrolysate, hemicellulosic hydrolysate, cellobiose and xylose, used alone or as a mixture. Highly preferably, said other carbonaceous substrate is selected from non-inducer sugars, highly preferably from glucose, cellulosic hydrolysate and hemicellulosic hydrolysate.

This mixture is termed the carbonaceous production substrate. Said carbonaceous production substrate contains at least 5% by weight of cellulose.

The carbonaceous production substrate is prepared in a concentration of 150 to 400 g of carbonaceous substrate per litre of carbonaceous production substrate. The specific flow rate at which the carbonaceous production substrate of production phase b) is supplied is advantageously in the range 35 to 65 mg of carbonaceous substrate per gram of microorganism per hour, preferably 35 to 45 mg of carbonaceous substrate per gram of microorganism per hour.

Said solid residue is obtained from the step for enzymatic hydrolysis of lignocellulosic materials which have undergone a pre-treatment step. Optionally, a solid residue obtained from the step for ethanolic fermentation of enzymatic hydrolysates is added.

The step for pre-treatment of lignocellulosic material can be used to improve the susceptibility of the cellulosic fraction to enzymatic hydrolysis. Preferably, the pre-treatment step is an acid pre-treatment step, preferably an acid hydrolysis, acid cooking or steam explosion step with prior impregnation of said material with an aqueous sulphuric acid solution. Preferably, the pre-treatment step is steam explosion.

At the end of the pre-treatment step, a solid residue may advantageously be separated from a liquid fraction containing sugars, termed a hemicellulosic hydrolysate, by liquid/solid separation. Said residue may also advantageously be used in phase b) for the production of an enzymatic cocktail of the invention as a carbonaceous inducer substrate. The carbonaceous inducer substrate used in the production phase b) may thus advantageously be separated at the end of the step for pre-treatment of a lignocellulosic material.

Preferably, said production phase b) is carried out for a period of more than at least 30 h, preferably more than at least 100 h.

Preferably, said production phase b) is operated at a pH in the range 3 to 5.5, and at a temperature in the range 20° C. to 30° C.

Said production phase b) may be carried out in fed-batch and chemostat modes, which are known to the skilled person.

In a preferred embodiment, the pre-treated lignocellulosic material is hydrolysed in an enzymatic hydrolysis step. The effluent from this step is then treated in a step for ethanolic fermentation of the monomeric sugars of the enzymatic hydrolysates. These treatments may be carried out in the same equipment or in different equipment. The solid residue is separated after the enzymatic hydrolysis step and/or after the ethanolic fermentation step.

In another preferred embodiment, the fermentation step and at least a portion of the hydrolysis step are carried out simultaneously. This is carried out, for example, by adding ethanolic yeasts during the hydrolysis step. The solid residue is separated at the end of the fermentation step.

The hydrolysis step is initiated by adding enzymatic cocktail. The quantity which is advantageously used is 1 to 60 mg of enzymatic cocktail per gram of cellulose in the lignocellulosic material which has undergone a pre-treatment step, preferably 5 to 35 mg of enzymatic cocktail per gram of cellulose in said material, and more preferably 5 to 20 mg of enzymatic cocktail per gram of cellulose in said material. Said hydrolysis step is carried out with 10% to 40% by weight of DM, preferably 15% to 25% by weight of DM.

The following examples illustrate the invention without limiting its scope.

EXAMPLE 1

Production of an Enzymatic Cocktail on Glucose
(Not in Accordance With the Invention)

An enzymatic cocktail was produced in a mechanically stirred reactor. The mineral medium (termed 4N) had the following composition: KOH 1.66 g/L, 85% $H_3PO_4$ 2 mL/L, $(NH_4)_2SO_4$ 2.8 g/L, $MgSO_4 \cdot 7 H_2O$ 0.6 g/L, $CaCl_2$ 0.6 g/L, $MnSO_4$ 3.2 mg/L, $ZnSO_4 \cdot 7 H_2O$ 2.8 mg/L, $CoCl_2$ 10 4.0 mg/L, $FeSO_4 \cdot 7 H_2O$ 10 mg/L, Corn Steep 1.2 g/L, antifoaming agent 0.5 mL/L.

Liquid Preculture

The microorganism (the *Trichoderma reesei* CL847 strain) was grown, by preculture using glucose as the carbonaceous growth substrate, at a concentration of 30 g/L. The mineral medium of the preculture was the 4N medium supplemented with 5 g/L potassium phthalate in order to buffer the pH. Inoculum growth lasted 3 days and was carried out at 30° C. in a stirred incubator. Transfer to the reactor was carried out if the residual glucose concentration was less than 15 g/L.

Growth Phase

The reactor containing the 4N medium was sterilized at 120° C. for 20 minutes. The glucose carbonaceous growth substrate was sterilized from 120° C. for 20 minutes then added to the reactor in a sterile manner so as to produce a concentration of 30 g/L. The reactor was inoculated to 10% (v/v) with the liquid preculture of the *Trichoderma reesei* CL847 strain. The operating conditions were a temperature of 27° C. and a pH of 4.8 (regulated using 5.5 M ammonia). Aeration was at 0.5 vvm and stirring was increased to between 200 and 800 rpm as a function of the $pO_2$ (pressure of dissolved oxygen), which was maintained at 30%.

Production Phase

When the carbonaceous growth substrate of the reactor was exhausted, the 250 g/L glucose carbonaceous production substrate was injected continuously at a flow rate of 35 mg per g of microorganism per hour, for 164 hours. The operating conditions were: a temperature of 25° C. and a pH of 4 (regulated with 5.5M ammonia, this latter also providing the nitrogen necessary for synthesis of the excreted proteins). The dissolved oxygen content was maintained at 30% by adjusting the stirring.

Production of the enzymatic cocktail was monitored by assaying extracellular proteins using the Lowry method and standard BSA after separating out the mycelium by filtering or centrifuging.

The analytical determinations carried out on the final must provided the following results:

| | |
|---|---|
| biomass (g/L) | 15.2 |
| proteins (g/L) | 2.9 |
| $q_p$ (mg/g/h) | 1.2 | where $q_p$ is the specific rate for the production of enzymatic cocktail.

EXAMPLE 2

Production of Enzymes on Lactose (Not in Accordance With the Invention)

Enzymatic cocktail was produced under the same conditions as in Example 1. The carbonaceous substrate for growth and production was pure lactose. Lactose is an important inducer in the production of enzymatic cocktail.

After 30 hours growth, after exhausting the carbonaceous growth substrate, the fed-batch solution, 250 g/L, was injected continuously at a flow rate of 35 mg of microorganism per hour, for 164 hours.

The analytical determinations carried out on the final must provided the following results:

| | |
|---|---|
| biomass (g/L) | 13.5 |
| proteins (g/L) | 37.8 |
| $q_p$ (mg/g/h) | 17 |

Induction of the production of enzymatic cocktail by lactose had clearly been observed (concentration of proteins and high $q_p$).

EXAMPLE 3

Inducer Effect of Solid Residue and of Various Carbonaceous Substrates

The study of the inducer effect of various carbonaceous substrates was carried out in flasks using the same preculture. The flasks were made up in duplicate and the carbonaceous production substrates used were: glucose (suppressor of enzymatic cocktail production), lactose (inducer), cellulose (inducer), and two different concentrations of solid hydrolysis residue. The solid residue was obtained from a partial hydrolysis (70%) of a wheat straw pre-treated by steam explosion under acidic conditions. This residue had been washed and compressed to 30% DM. It had the following compositions: 19% cellulose, 59% lignin, 2.9% hemicelluloses, 0.6% acetyls, 11% ash, 7.5% nd (not determined)

Growth of the fungus *T. reesei* under preculture was carried out on glucose at a concentration of 10 g/L. Growth of the inoculum lasted 3 days and was carried out at 30° C. in an Infors incubator, with stirring (150 rpm), in two Fernbach flasks with a useful volume of 350 mL. The two flasks were mixed at the end of preculture. The residual glucose concentration was 0.3 g/L.

The composition of the flasks is detailed in Table 1. They were sterilized before inoculation.

TABLE 1

| Flask composition | Control | Solid residue (1 g) | | Solid residue (4 g) | | Glucose | | Lactose | | Cellulose | |
|---|---|---|---|---|---|---|---|---|---|---|---|
| | Flask 0 | Flask 1 | Flask 2 | Flask 3 | Flask 4 | Flask 5 | Flask 6 | Flask 7 | Flask 8 | Flask 9 | Flask 10 |
| Saline medium 4N (mL) | 25 | 25 | 25 | 25 | 25 | 25 | 25 | 25 | 25 | 25 | 25 |
| Potassium phthalate (g) | 0.6 | 0.6 | 0.6 | 0.6 | 0.6 | 0.6 | 0.6 | 0.6 | 0.6 | 0.6 | 0.6 |
| Yeast extract (g) | 0.1 | 0.1 | 0.1 | 0.1 | 0.1 | 0.1 | 0.1 | 0.1 | 0.1 | 0.1 | 0.1 |
| Material obtained from hydrolysis, H10 (g) | 0 | 1 | 1 | 4 | 4 | 0 | 0 | 0 | 0 | 0 | 0 |
| Glucose, 200 g/L (mL) | 0 | 0 | 0 | 0 | 0 | 5 | 5 | 0 | 0 | 0 | 0 |
| Lactose, 200 g/L (mL) | 0 | 0 | 0 | 0 | 0 | 0 | 0 | 5 | 5 | 0 | 0 |
| Cellulose:Nutrafiber (g) | 0 | 0 | 0 | 0 | 0 | 0 | 0 | 0 | 0 | 1 | 1 |
| Water (mL) | 25 | 25 | 25 | 25 | 25 | 20 | 20 | 20 | 20 | 25 | 25 |
| Inoculation (mL) | 50 | 50 | 50 | 50 | 50 | 50 | 50 | 50 | 50 | 50 | 50 |

The flasks were incubated in an Infors incubator at 30° C. and with stirring (150 rpm). The analytical determinations on the final must (after 94 h) produced the following results:

|        | Concentration of proteins | qp (mg/g/h) |
|--------|---------------------------|-------------|
| Flask 0  | 1.02 | 0.10  |
| Flask 1  | 1.95 | 3.92  |
| Flask 2  | 2.09 | 4.52  |
| Flask 3  | 2.52 | 6.31  |
| Flask 4  | 2.39 | 5.75  |
| Flask 5  | 0.97 | −0.12 |
| Flask 6  | 0.97 | −0.13 |
| Flask 7  | 3.02 | 8.35  |
| Flask 8  | 2.81 | 7.51  |
| Flask 9  | 2.47 | 6.10  |
| Flask 10 | 2.43 | 5.90  |

The control and the flasks using the glucose were at a concentration of 1 g/L, which probably corresponded to the concentration of the yeast extract. The mean qp of these flasks was close to 0. The flask with the lactose finished with a concentration of proteins of 3 g/L. The concentration of proteins with the cellulose and the 4 g of solid residue was 2.5 g/L. It was 2 g/L with 1 g of solid residue. This experiment demonstrated induction, by the solid residue, of the production of enzymatic cocktail at a level comparable to cellulose alone, and despite the presence of lignin.

The invention claimed is:

1. A process for the production of an enzymatic cocktail with a cellulolytic microorganism, comprising two phases:
   a phase a) comprising growing said microorganism in the presence of at least one carbonaceous growth substrate in a closed reactor, said phase a) being carried out with a concentration of carbonaceous growth substrate in the range of 10 to 90 g/L; and
   a phase b) comprising producing the enzymatic cocktail, in which at least one carbonaceous inducer substrate is supplied to the reactor, said carbonaceous inducer substrate being at least one solid residue obtained by enzymatic partial hydrolysis of lignocellulosic materials which have undergone a pre-treatment step, said solid residue having a liquid portion and a solid portion wherein the solid portion constitutes 10% to 40% by weight of the solid residue and said solid residue having no solid residue obtained from ethanolic fermentation of enzymatic hydrolysates from the enzymatic partial hydrolysis of lignocellulosic materials which have undergone a pre-treatment step, said phase b) being carried out with a concentration of carbonaceous inducer substrate in the range of 150 to 400 g/L, wherein the partial hydrolysis is conducted with an initial enzymatic cocktail, wherein, in the partial hydrolysis, only 20% to 70% by weight of the lignocellulosic materials subject to the enzymatic partial hydrolysis are hydrolysed and wherein the partial hydrolysis is conducted with:
   a dry matter content of more than 20% by weight; and/or
   with less than 10 mg of the initial enzymatic cocktail per gram of cellulose in the lignocellulosic materials which have undergone a pre-treatment step.

2. The process according to claim 1, in which the portion of lignin in the solid portion of said solid residue is 45% to 80% by weight.

3. The process according to claim 1, in which said solid residue is separated from the effluent of the enzymatic partial hydrolysis.

4. The process according to claim 1, in which said carbonaceous inducer substrate is used as a mixture with at least one other carbonaceous substrate selected from the group consisting of inducer and non-inducer sugars.

5. The process according to claim 4, in which said other carbonaceous substrate is selected from the group consisting of lactose, glucose, cellulosic hydrolysate, hemicellulosic hydrolysate, cellobiose and xylose, used alone or as a mixture.

6. The process according to claim 1, in which the carbonaceous inducer substrate contains at least 5% by weight of cellulose.

7. The process according to claim 1, in which the specific flow rate at which the carbonaceous inducer substrate used in said phase b) is supplied is in the range of 35 to 65 mg of carbonaceous inducer substrate per gram of microorganism per hour.

8. The process according to claim 1, in which said carbonaceous inducer substrate is separated after the pre-treatment of the lignocellulosic materials.

9. The process according to claim 1, in which said partial hydrolysis is initiated with an amount of initial enzymatic cocktail in the range of from 1 mg to less than 10 mg per gram of cellulose in the lignocellulosic materials which have undergone a pre-treatment step.

10. The process according to claim 9, in which said partial hydrolysis is carried out with an amount of dry matter in the range of from more than 20% to 40% by weight.

11. The process according to claim 1, in which the cellulolytic microorganism is selected from the group consisting of strains of fungi belonging to the genuses *Trichoderma, Aspergillus, Penicillium* and *Schizophyllum*.

12. The process according to claim 11, in which the cellulolytic microorganism belongs to the species *Trichoderma reesei*.

13. The process according to claim 1, wherein the pre-treatment step which the lignocellulosic materials have undergone is an acid pre-treatment step.

14. The process according to claim 1, wherein the pre-treatment step which the lignocellulosic materials have undergone is a steam explosion step with prior impregnation of said materials with an aqueous sulphuric acid solution.

* * * * *